United States Patent [19]

Crossley et al.

[11] Patent Number: 5,708,026

[45] Date of Patent: Jan. 13, 1998

[54] CYCLOHEXANE DERIVATIVES

[75] Inventors: Roger Crossley, Reading; Albert Opalko, Maidenhead, both of England

[73] Assignee: John Wyeth & Brother, England

[21] Appl. No.: 448,470

[22] PCT Filed: Feb. 10, 1995

[86] PCT No.: PCT/GB95/00280

§ 371 Date: Jul. 15, 1996

§ 102(e) Date: Jul. 15, 1996

[87] PCT Pub. No.: WO95/21813

PCT Pub. Date: Aug. 17, 1995

[30] Foreign Application Priority Data

Feb. 10, 1994 [GB] United Kingdom ............ 9402561
Dec. 15, 1994 [GB] United Kingdom ............ 9425351

[51] Int. Cl.$^6$ ............ A61K 31/24; A61K 31/135; C07C 229/34; C07C 211/25

[52] U.S. Cl. ............ 514/539; 514/647; 560/43; 564/336

[58] Field of Search ............ 560/43; 564/336; 514/539, 647

[56] References Cited

FOREIGN PATENT DOCUMENTS

| | | | |
|---|---|---|---|
| 3231912 | 1/1984 | Germany | C07C 87/50 |
| 3231911 | 3/1984 | Germany | C07C 87/50 |
| 3245320 | 6/1984 | Germany | C07C 119/048 |
| 3245321 | 6/1984 | Germany | C07C 119/048 |
| 3414803 | 10/1985 | Germany | C07C 87/50 |
| 0764633 | 12/1956 | United Kingdom . | |

OTHER PUBLICATIONS

Egli et la, Helv. Chim. Acta. 58 (8), 2321–2346 (1975).

*Primary Examiner*—Joseph Conrad
*Attorney, Agent, or Firm*—R. F. Boswell, Jr.

[57] ABSTRACT

This invention concerns compounds of generic formula:

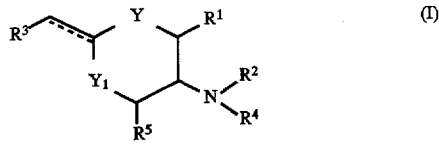

(I)

or a pharmaceutically acceptable salt thereof, where the dotted line represents an optional bond, one of $R^1$ and $R^5$ represents hydrogen, $C_1$–$C_6$ alkyl, $C_7$–$C_{16}$ aralkyl, —$(CHR^6)_n CHR^7 CN$, —$(CHR^6)_n CHR^7 CONH_2$, —$(CHR^6)_n CHR^7 COOR^8$, —$(CHR^6)_n CHR^7 CH_2 OH$ wherein n is 0 or 1, $R^6$ and $R^7$ independently represent hydrogen, $C_1$–$C_6$ alkyl- or $C_7$–$C_{16}$ aralkyl-, and $R^7$ also represents hydroxy($C_1$–$C_6$)alkyl-, ($C_2$–$C_7$)alkanoyloxy($C_1$–$C_6$)alkyl-, ($C_1$–$C_6$ alkoxy) carbonyl- and $R^8$ is hydrogen or $C_1$–$C_6$ alkyl;

the other of $R^1$ and $R^5$ is hydrogen, $C_1$–$C_6$ alkyl or $C_7$–$C_{16}$ aralkyl; $R^3$ is $C_6$–$C_{10}$ aryl or heteroaryl group optionally substituted by one or more substituents the same or differnet, $R^2$ and $R^4$ independently represent hydrogen, or a group of formula —$CR^a R^b R^c$ where $R^a$, $R^b$ and $R^c$ are independently selected from hydrogen, $C_1$–$C_6$ alkyl, optionally substituted $C_6$–$C_{10}$ aryl, optionally substituted heteroaryl, $C_1$–$C_6$ alkyl substituted by optionally substituted $C_6$–$C_{10}$ aryl or heteroaryl or $R^2$ also represents $COR^{11}$ where $R^{11}$ is $C_1$–$C_6$ alkyl, $C_1$–$C_6$ alkoxy or an optionally substituted ($C_6$–$C_{10}$ aryl)alkyl or a heteroaryl alkyl radical; one of Y and $Y_1$ is

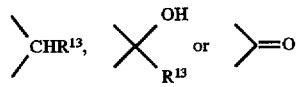

where $R^{13}$ represents hydrogen, $C_1$–$C_6$ alkyl or $C_7$–$C_{16}$ aralkyl; the other of Y and $Y_1$ is —$CHR^{12}$— where $R^{12}$ is hydrogen, $C_1$–$C_6$ alkyl or $C_7$–$C_{16}$ aralkyl, which compounds have pharmaceutical uses conferred by their ability to block voltage gated potassium channels.

15 Claims, No Drawings

CYCLOHEXANE DERIVATIVES

This invention relates to cyclohexane derivatives more particularly to substituted aminocyclohexanes, to processes for preparing them to pharmaceutical compositions containing them. The compounds have pharmaceutical uses conferred by their ability to block voltage gated potassium channels and they are also useful as intermediates to nitrogen heterocycles which are potassium channel blockers.

Voltage gated potassium ion ($K^+$) channels which produce transient outward currents (TOC) are present in the cell membranes of neurones and serve to repolarise the cell following a depolarisation by opening and allowing potassium ions to flow from the inside of the cell to the outside. They are, therefore, one of the main regulating influences on the nerve cell firing and determine the amount of current reaching the terminal regions of the cells. This in turn regulates the amount of neurotransmitter substances released from the nerve terminals. In addition, they help to determine the refractory period of the nerve cell and hence the probability of the cell firing again within a certain time. This governs neuronal excitability and also the tendency of a cell to undergo repetitive firing. An ability to modify the functioning of these channels by chemical means is likely to produce therapeutically useful agents. So far the agents which are known to block the TOC channels are toxins such as the snake toxin dendrotoxin, or 4-aminopyridine and its derivatives. Blockade of the TOC channels leads to a change in the pattern of transmitter release and depending upon the pattern and type of neurone affected different therapeutic ends will result. For example TOC blockers which increase dopaminergic transmission in the substantia nigra will be of use in treatment of Parkinson's disease. Likewise, an increase in cholinergic function is of use in Alzheimer's disease and in cognition enhancement. Because of the complicated neural networks in the brain blockade of the TOC may also lead to increase in more than one transmitter substance at a time and this can act synergistically where a disease state is associated with more than one transmitter deficit as is often the case. It is evident, therefore that TOC blockers may be of use in areas of depression, pain, psychoses, cognition, memory and learning, anxiety, Parkinson's disease and Alzheimer's disease. In addition they can be used as a treatment for conditions where there is an impairment of nerve transmission such as multiple sclerosis.

Compounds which act to increase channel function may be termed channel openers and these serve to increase the braking action of the channels on the cells. In this respect they will also reduce the likelihood of the cells to undergo repetitive firing and may be used as anticonvulsants in the treatment of epilepsy. Also, their action to reduce neurotransmitter release means that they may be used as anaesthetics, analgesics, sedatives and anxiolytics.

This invention provides compounds of generic formula (I):

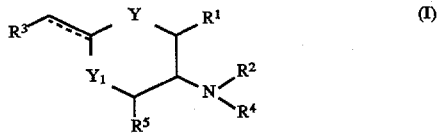

or a pharmaceutically acceptable salt thereof, where the dotted line represents an optional bond, one of $R^1$ and $R^5$ represents hydrogen, $C_1-C_6$ alkyl, $C_7-C_{16}$ alkyl, $-(CHR^6)_n CHR^7 CN$, $-(CHR^6)_n CHR^7 CONH_2$, $-(CHR^6)_n CHR^7 COOR^8$, $-(CHR^6)_n CHR^7 CH_2 OH$ wherein n is 0 or 1, $R^6$ and $R^7$ independently represent hydrogen, $C_1-C_6$ alkyl- or $C_7-C_{16}$ alkyl-, and $R^7$ also represents hydroxy($C_1-C_6$)alkyl-, ($C_2-C_7$)alkanoyloxy($C_1-C_6$)alkyl-, ($C_1-C_6$alkoxy)carbonyl- and $R^8$ is hydrogen or $C_1-C_6$ akyl;

the other of $R^1$ and $R^5$ is hydrogen, $C_1-C_6$ alkyl or $C_7-C_{16}$ akyl;

$R^3$ is an optionally substituted $C_6-C_{10}$ aryl or heteroaryl group; said heteroaryl group containing 5 to 10 ring atoms of which one or more (e.g up to 3) of said atoms are heteroatoms selected from oxygen, nitrogen and sulphur, the same or different; said aryl or heteroaryl radicals being optionally substituted by one or more substituents the same or different, eg substituents commonly used in pharmaceutical chemistry such as for example: $C_1-C_6$ alkyl; $C_1-C_6$ alkoxy or such groups substituted by $C_6-C_{10}$ aryl or heteroaryl as defined above; halogen; halo$C_1-C_6$alkyl; halo$C_1-C_6$alkoxy; carboxy; hydroxy($C_1-C_6$)alkyl; ($C_1-C_6$alkoxy) carbonyl; amino including substituted amino, e.g mono- or di- ($C_1-C_6$ alkyl)-amino; nitro; hydroxy; mercapto; $C_1-C_6$alkylthio; ($C_1-C_6$)alkyl carbonyl; ($C_6-C_{10}$ aryl) carbonyl; ($C_2-C_7$)alkanoyloxy: ($C_7-C_{11}$)aroyloxy; ($C_1-C_6$)alkylcarbonylamino, ($C_6-C_{10}$aryl) carbonylamino; ($C_2-C_7$) alkoxycarbonylamino; $C_6-C_{10}$ aryl; heteroaryl as defined above; or $C_1-C_2$ alkylenedioxy;

$R^2$ and $R^4$ independently represent hydrogen, or a group of formula $-CR^a R^b R^c$ where $R^a$, $R^b$ and $R^c$ are independently selected from hydrogen, $C_1-C_6$ alkyl, optionally substituted $C_6-C_{10}$ aryl, optionally substituted heteroaryl, $C_1-C_6$ alkyl substituted by optionally substituted $C_6-C_{10}$ aryl or heteroaryl in which the substituent(s) is/are for example as illustrated above in connection with $R^3$; or $R^2$ also represents $COR^{11}$ where $R^{11}$ is $C_1-C_6$ alkyl, $C_1-C_6$ alkoxy or an optionally substituted ($C_6-C_{10}$ aryl)alkyl or a heteroaryl alkyl radical: said heteroaryl group containing 5 to 10 ring atoms of which one or more (e.g up to 3) of said atoms are heteroatoms selected from oxygen, nitrogen and sulphur, the same or different; said aryl or heteroaryl radicals being optionally substituted by one or more substituents the same or different, eg substituents commonly used in pharmaceutical chemistry such as for example: $C_1-C_6$ alkyl, $C_1-C_6$ alkoxy, or such groups substituted by $C_6-C_{10}$ aryl or heteroaryl as defined above: halogen; halo $C_1-C_6$ alkyl, halo $C_1-C_6$ alkoxy; carboxy; hydroxy($C_1-C_6$)alkyl $C_2-C_7$ alkanoyloxy ($C_1-C_6$)alkyl; ($C_1-C_6$alkoxy)carbonyl; amino including substituted amino, e.g mono- or di- ($C_1-C_6$ alkyl)-amino; nitro; hydroxy; mercapto; $C_1-C_6$alkyhhio; ($C_1-C_6$alkyl)carbonyl; ($C_6-C_{10}$ aryl) carbonyl: ($C_2-C_7$)alkanoyloxy; ($C_7-C_{11}$)aroyloxy; ($C_1-C_6$alkyl)carbonylamino, ($C_6-C_{10}$aryl) carbonylamino; ($C_2-C_7$ alkoxycarbonyl)amino; $C_6-C_{10}$ aryl; heteroaryl as defined above; or $C_1-C_2$ alkylenedioxy;

one of Y and $Y_1$ is

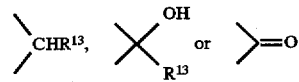

where $R^{13}$ represents hydrogen, $C_1-C_6$ alkyl or $C_7-C_{16}$ aralkyl;

the other of Y and $Y_1$ is $-CHR^{12}-$ where $R^{12}$ is hydrogen, $C_1-C_6$ alkyl or $C_7-C_{16}$ aralkyl.

As used herein, examples of alkyl as a group or part of a group, e.g aralkyl, alkanoyl, are straight or branched chain groups of up to 6 carbon atoms especially of 1 to 4 carbon atoms such as methyl, ethyl, n-propyl, isopropyl, n-butyl and sec butyl. Examples of "alkoxy" as a group or part of a group, e.g alkoxycarbonyl, are groups of formula alkyl-O- where alkyl has the meanings immediately above. Examples of aryl as a group or part of a group, e.g aralkyl, aralkanoyl, are mono- or bicyclic groups of 6 to 10 carbon atoms such as phenyl and naphthyl, e.g 1 or 2-naphthyl. Heteroaryl groups have heteroatoms selected from oxygen, nitrogen and/or sulphur. Examples of heteroaryl as a group or part of a group, e.g heteroarylalkyl, are mono- or bicyclic groups of 5 to 10 ring atoms such as those having one nitrogen heteroatom e.g 2 or 3-pyrrolyl, 2, 3 or 4-pyridyl, quinolyl (e.g 2, 3 or 6-quinolyl) isoquinolyl (e.g 1-, 3- or 6-isoquinolyl); one sulphur atom, e.g 2- or 3-thienyl or benzothienyl (e.g 2, 3 or 6-benzothienyl); or one oxygen atom, e.g 2- or 3-furanyl or benzofuranyl (e.g 2-, 3- or 6-benzofuranyl); or two or more heteroatoms e.g thiazolyl (e.g 2-thiazolyl), imidazolyl (e.g 2-imidazolyl); oxazolyl (e.g 2-oxazolyl).

$R^3$ may be for example phenyl or phenyl substituted by one or more substituents as illustrated above, e.g substituents the same or different selected from: $C_1$–$C_6$ alkoxy such as methoxy, ethoxy; halogen such as chlorine or bromine; $CF_3$; $CF_3O$; $C_1$–$C_6$ alkyl such as methyl or ethyl; hydroxy; cyano and carboxy. Preferred values for $R^3$ are methoxyphenyl, e.g 4-methoxyphenyl and hydroxyphenyl, e.g 4-hydroxyphenyl.

Examples of the group Y (and $Y_1$) are $CH_2$, CO and CHOH.

The values of $R^4$ and $R^2$ are for example hydrogen or a group of formula —$CR^aR^bR^c$ where $R^a$ and $R^b$ are independently selected from hydrogen, methyl ethyl, propyl, isopropyl or butyl and $R^c$ is selected from hydrogen, methyl, ethyl, isopropyl, propyl, butyl or a $C_6$–$C_{10}$ aryl or a heteroaryl group containing 5–10 ring atoms of which one or more of said atoms are heteroatoms selected from oxygen, nitrogen and sulphur in which said aryl and heteroaryl moieties are optionally substituted as illustrated above.

Preferably $R^2$ is hydrogen and $R^4$ is —$CR^aR^bR^c$ where $R^a$ is hydrogen, $R^b$ is methyl and $R^c$ is optionally substituted aryl such as phenyl or substituted phenyl such as illustrated above. $R^2$ may also be $COCH_3$, $COOCH_3$ or $COCH_2Ph$.

Preferred compounds of formula I have $R^3$ represents 4-methoxyphenyl. Also preferred are compounds where $R^2$ represents methyl or hydrogen.

Examples of $R^1$ and $R^5$ are hydrogen, Me, Et, "Pr, benzyl, —$(CH_2)_2OH$, —$CH_2CH_2CN$, —$(CH_2)_2COOMe$, and —$(CH_2)_2COOEt$.

Particularly preferred are compounds of formula IA:

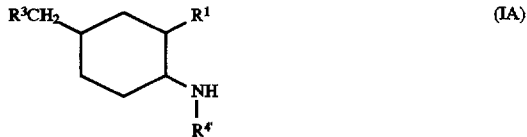

(IA)

in which formula $R^1$ is hydrogen, $C_1$–$C_6$ alkyl, or $CH_2CH_2COOR^8$; $R^3$ is as defined above, preferably unsubstituted or substituted phenyl. e.g where the substituents is/are selected from $C_1$–$C_6$ alkyl, $C_1$–$C_6$ alkoxy, hydroxy, halogen and methylene or ethylene-dioxy; $R^{4'}$ is hydrogen, alkyl or optionally substituted aryl($C_1$–$C_6$) alkyl in which the alkyl group is itself optionally substituted by $C_1$–$C_6$ alkyl, and $R^8$ is hydrogen or $C_1$–$C_6$ alkyl.

Examples of $R^{4'}$ include phenylmethyl or α-methylphenylmethyl in which the phenyl group is optionally substituted by substituents as listed above.

Preferred values for $R^{4'}$ are PhCH(Me)—, $PhCH_2$— and H.

The compounds of formula I can possess one or more asymmetric centres and accordingly the compounds may exist and be isolated in a number of optically active stereoisomeric foes. Geometric isomers (,e.g. E and Z; cis and trans) are also obtained when $R^3$ is bonded via a double bond. This invention encompasses the compounds of formula I in any optically active or geometric form or mixtures thereof eg, racemates or diastereoisomers. Standard separation techniques may be used to isolate particular enantiomeric and diastereomeric forms. For example a racetalc mixture may be converted to a mixture of optically active diastereoisomers by reaction with a single enantiomer of a 'resolving agent' (for example by diastereomeric salt formation or formation of a covalent bond). The resulting mixture of optically active diastereoisomers may be separated by standard techniques (e.g crystallisation or chromatography) and individual optically active diastereoisomers then treated to remove the 'resolving agent' thereby releasing the single enantiomer of the compound of the invention. Chiral chromatography (using a chiral support, eluent or ion pairing agent) may also be used to separate enantiomeric mixtures directly.

Stereospecific synthesis using optically active starting materials and/or chiral reagent catalyst and/or solvents may also be employed to prepare particular diastereoisomers or even a particular enantiomer.

The compounds of formula I possess pharmacological activity in particular they block voltage gated potassium chanels. They may therefore be used to treat CNS disorders as described above such as depression, pain psychoses, anxiety, movement disorders (such as Parkinson's disease) and multiple sclerosis and in enhancing cognition, memory and learning. They demonstrate their ability to block voltage gated potassium channels in dorsal root ganglion cells by the following standard test procedures:

PROCEDURE 1

Modulation of voltage-activated K+ currents in dorsal root ganglion (DRG) cells:

The method used in the culture or dorsal root ganglion cells is similar to that described by Wood el. at., Capsaicin induced ion fluxes in dorsal root ganglion cells in culture, J. Neuroscience, 8, 3208–3220) (1988L Dorsal root ganglia are dissected mainly from around the lumbar and thoracic vertebrae and placed in a conical centrifuge tube containing Ham's F14 nutrient mixture (F14:Imperial Laboratories) plus horse serum (HS: GIBCO or Flow). When all ganglia have been collected (ex ca. 14 pups) the excess medium is removed and the ganglia incubated for 30 min in "F14+HS" containing 0.1% collagenase Type 1A-S (Sigma). Excess medium is removed, ganglia washed in 4 ml F14 (no HS), resuspended and spun down at 900 g for 10 s. The supernatant is again removed and replaced with 1.8 ml F14 (no HS) plus 0.2 ml trypsin (GIBCO) at a final concentration of 0.25%. The ganglia are then incubated at 37° C. for 30 min agitating every 10 min to prevent clumping. The trypsinisation is inhibited by the addition of 6 ml "F14+HS" and cells are resuspended and centrifuged as before. The medium is removed and 2 ml added of "F14 +HS" containing 0.4% DNAase 1 (Sigma). The ganglia are then triturated gently 15–20× using a siliconised pasteur pipette, filtered through a 90 mm nylon mesh filter and collected into a centrifuge tube. The filter is further washed with 2 ml of "F14 +HS" which is collected into the same tube. The suspension is spun at 900 g for 3 min, the supernalant removed and the cells resuspended in DRG Growth Medium (DRG-GM) which consists of: HAMS F14 nutrient mixture (40%, v/v), HS(10%, v/v) C6 conditioned medium (50%, v/v), penicillin/streptomycin (100U/ml; 100 μg/ml) and NGF (30 μg/ml). Cells are then plated out onto five 60mm poly-L-lysine-coated tissue culture petri dishes (see below).

Replating

After a few days in culture (3–7 days, usually), cells are resuspended from 60 mm dishes using a 0.25% solution of trypsin in F14. An equal volume of DRG-GM is added to inhibit the trypsin, the cells are spun at 900 g for 5 minutes and resuspended in 0.25–0.5 ml of DRG-GM. Neurites are removed by gentle trituration through a 21 g syringe needle (15–20 strokes) and a drop of the cell suspension is then placed on each of 5–6 poly-D-lysine- and laminin-coated 35 mm petri dishes (see below). After 30 minutes incubation at 37° C., each plate is flooded with ca 1.5 ml DRG-GM and after about 1 hour incubation, cells are ready for electrophysiological recording. This final step is carried out specifically in order to remove neurites which hinder good voltage-clamp of the cells.

Coating of plates

2ml of poly-D-lysine (Sigma), reconsitituted in distilled water to 100 μg/ml, are added to each plate and left for 1–2 hours. Plates are then washed with water and left to dry. Laminin (5 μg/ml) is added as a drop to the centre of plates (previously coated with poly-D-Lys), left for 45 min before removal of excess and use of plates.

Electrophysiology

Recordings are made using an AxoClamp-2A (Axon Instruments Inc) switiching damp amplifier using patch electrodes (4–8M ohms), made from borosilicate glass capillary tubes (GC150TF-10, Clark Electromedical) and fire-polished. Electrodes are filled with (in mM): 140K Gluconate, 2 $MgCl_2$, 1.1 EGTA/KOH, 5 HEPES, 20 sucrose, 2 MgATP, 0.2 GTP; pH set to 7.2 with KOH and osmolarity adjusted with sucrose to 310 mOsm. The electrodes are then and dipped in Sigmacote (Sigma) prior to recording to reduce stray capacitance. The bathing solution in which cells are continually perfused (during recordings) consists of (in mM): 124 NaCl, 2.5 KCl 4 $MgCl_2$. 5 HEPES, 10 glucose, 1 μM TTX, 20 sucrose pH set to 7.4 with NaOH and osmolarity adjusted with sucrose to 320 mOsm. $Ca^{2+}$ is omitted from the bathing medium in order to miniraise voltage-activated $Ca^{2+}$ currents and $Ca^{2+}$ activated K+ currents. TTX is included to block voltage-activated $Na^+$ currents, although in some recordings a residual TTX-resistant $Na^+$ current is evident. Recordings are made in voltage-clamp mode using a voltage-step protocol consisting of:

i) holding potential ($V_h$)=−30 mV (in order to inactivate transient outward current)

ii) 1 s prepulse to −100 mV iii) 1 s pulse to +60 mV to activate total outward current iv) return to −30 mV In some cases current-voltage (I–V) relationships are obtained in the presence and absence of test compound by constructing families of voltage steps over a range of membrane potentials (−100 mV to +60 mV) from a holding potential of either −30 mV or −100 mV. Voltage steps and data acquisition (current responses) are controlled by an Atari MegaSTE computer interfaced to the voltage-clamp via an ITC-16 ADC/DAC (Instrutech Corp.) and subsequent analysis carried out using REVIEW (Instrutech Corp). Test compounds are applied to individual neurones by a local microperfusion system, initially at a test concentration of 10 μM (solubility-permitting).

CALCULATIONS

Current responses during the test voltage step to +60 mV (above) are measured off-line using REVIEW (Instrutech Corp). The following measurements are made:

peak (with ca.50 ms) and Q integral (t=1 s) outward current measured at +60 mV:
  i) after conditioning prepulse to −100 mV (includes noninactivating as well as transient outward current (TOC)
  ii) without conditioning prepulse (mainly non-inactivating current)
  iii) difference (digital subtraction) of above currents corresponds to TOC).

Current amplitudes are obtained for: total outward current ($K_{-100}$) noninactivating current ($K_{-30}$) and TOC. Peak current amplitudes recorded in the presence of test compounds are expressed as a percentage of the corresponding control values.

Standard Compounds 4-aminopyridine ( 100% block of TOC at 1 mM) Toxin I (50% block of TOC at 100 mM) (Toxin I is a dendrotoxin homologue.)

PROCEDURE 2

Compounds of this invention were tested for blocking activity on the MK-1 voltage-activated K+ channel; according to the following standard test procedure:

CHO cells stably transfected with cDNA for MK-1 (Dr B Tempel et. al University of Washington, Nature, 332, 837–839 (1988)) were maintained in tissue culture using standard procedures and media for this cell line. Cells were plated on 35 mm plastic dishes and used subsequently for electrophysiology within 3 days.

Currents were recorded using the whole-cell voltage-clamp configuration of the patch clamp technique, using an Axopatch IC amplifier (Axon Instruments). Patch electrodes were manufactured from aluminosilicate glass tubing and heat polished prior to use. No electrode coating was necessary for whole-cell recording. Signal acquisition and analysis was performed using pClamp software (Axon Instruments). A p/4 subtraction procedure was used to remove leak and capacitive currents on line. A holding potential of −100mV was routinely used.

Two main protocols were used in testing drugs. 1) Current-voltage (I–V) curves were collected, with incrementing steps of either 10 or 20 mV. Full I–V curves were obtained both in control and drug solutions. 2) A 'pharmacology' programme, which involved single voltage steps from −100 mV to +60 mV, applied and collected at 20 s intervals. Compounds under investigation were applied via a 'U' tube rapid perfusion system to a small area of the recording chamber. Drug applications were always bracketed by control solutions to ensure reversibility. The recording chamber was continuously perfused at 3 ml.min$^{-1}$. Results are expressed as % of control peak current (at +60 mV). However, where drugs have a time dependent effect on MK- 1. i.e acceleration of decay, results are also expressed as a % of total charge transferred within the duration of the voltage step.

The standard extracellular solution contained (in mM): NaCl 135, KCl 5, $MgCl_2$ 4, EGTA 1, HEPES 10 and glucose 25, set to pH 7.4 with NaOH. The intracellular (pipette)

solution comprised: K aspartate/K gluconate 120, KCl 20, MgCl$_2$, MgATP 2, EGTA 10, HEPES 10, pH at 7.4 with NaOH. This solution was stored in 1 ml aliquots at –4° C., and filtered at 0.2mm. The MK-1 current is a slowly rising, very slowly inactivating current, which may reach several nA in amplitude at +60 mV.

| STANDARD COMPOUNDS: | | |
|---|---|---|
| Compound | Concentration | % Peak Control Current |
| 4-aminopyridine | 0.1 mM | 36 |
| 4-aminopyridine | 2 mM | 91 |
| Tetraethylammonium | 10 mM | 92 |
| Toxin I | 100 nM | 90 |
| Quinine | 100 μM | 75 |

RESULTS

Results for representative compounds of this invention in the two abovementioned tests are shown in the Table below:

| COMPOUND | | % Block of TOC | |
|---|---|---|---|
| EXAMPLE NO | CONCEN- TRATION | PROCEDURE 1 DRG % | PROCEDURE 2 mKv 1.1 (CHO) % |
| 1 | 10 μM | — | 33 |
| 2 | 10 μM | 18 | — |
| 3 | 10 μM | — | 50 |
| 5A | 10 μM | — | 52 |
| 5B | 10 μM | — | 46 |

The results show the ability of compounds of this invention to block voltage gated potassium channels in cells indicating pharmaceutical uses as described hereinabove.

This invention also provides processes for preparing the compounds formula I and IA.

Many starting materials used herein can be derived from substituted catechols, reduced to give or form many known cyclohexane-1,3- or -1,4-diones appropriately protected to give compounds of the type:

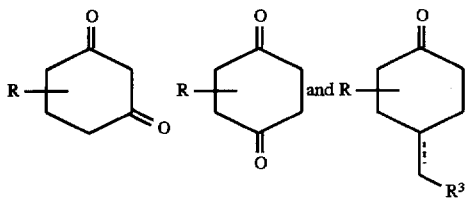

where R is $R^1$, $R^5$, $R^{12}$ or $R^{13}$ or a group convertible thereto, and $R^3$ is as defined herein.

The group R may be introduced into the ring via alkylation procedures treatment with lithium and a halide, such as an alkyl halide.

Compounds of formula I may be prepared by one of the following processes where if necessary reactive substituent groups are protected prior to reaction and removed thereafter; said processes comprising:

(A) reacting a compound of formula:

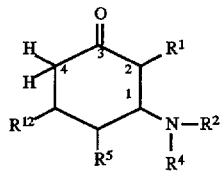

(II)

wherein $R^1$, $R^2$, $R^4$, $R^5$ and $R^{12}$ are as defined herein, with an aldehyde of formula $R^3$CHO, in the presence of base to give a corresponding compound of formula I which has oxo group in the 3-position and the optional bond to to the 4-position is present or (B) reacting a compound of formula:

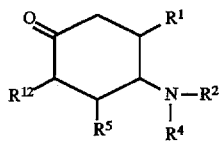

(III)

wherein $R^1$, $R^2$, $R^4$, $R^{12}$ and $R^{13}$ and $R^5$ are as defined above with an anion of formula:

$R^3CH_2^{\ominus}$ where $R^3$ is as defined above, e.g using a Grignard reagent, to give a corresponding compound of formula I having a 4-hydroxy group, which compound may be dehydrated to give a compound of formula I wherein the optional bond to the 4-position is present; or (C) reacting a compound of formula (III) as defined above with a Wittig reagent of formula:

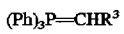

$(Ph)_3P=CHR^3$ wherein $R^3$ is as defined above to give a corresponding compound of formula I where the optional bond to the 4-position is present; or (D) reacting a compound of formula (IV):

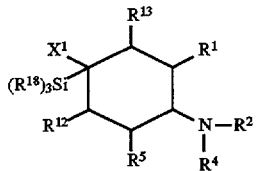

(IV)

wherein $R^1$, $R^2$, $R^4$, $R^5$, $R^{12}$ and $R^{13}$ are as defined above, $(R^{18})_3$ is defined as three $R^{18}$ radicals the same or different selected from alkyl, cycloalkyl, aralkyl, aryl or electron donating substituents such as alkoxy, cycloalkoxy, aralkoxy, aryloxy, alkylthio, cycloalkythio, aralkylthio or arylthio, the group $R^dR^eN$— where $R^d$ and $R^e$ are selected from alkyl, cycloalkyl, aryl and aralkyl or $R^d$ and $R^e$ are joined to form a heterocyclic ring with the nitrogen atom to which they are attached (e.g piperidinyl, pyrrolidinyl which may be substituted, e.g by alkyl) and $X^1$ is sodium, potassium or lithium, with a compound of formula:

$R^3CHO$ wherein $R^3$ is as defined above in connection with formula I; followed by treatment under acidic or basic conditions, to give a compound of formula I in which the optional bond to the 4-position is present; or (E) reacting a compound of formula (III) as defined above with a compound of formula:

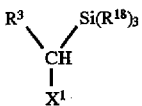
(V)

where $R^3$, $R^{18}$ and $X^1$ are as defined above, followed by treatment under acidic or basic conditions, or (F) converting a compound of formula I having at least one reactive site or substituent group to give a different compound of formula I; or (G) reducing a compound of formula (VI):

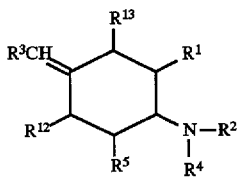
(VI)

wherein $R^1$, $R^2$, $R^3$, $R^4$ and $R^5$ are as defined above, e.g catalytically using 5% Pd/C and hydrogen: to give a saturated compound of formula I: or (H) converting a basic compound of formula I to an acid addition or quaternary ammonium salt thereof, or vice versa, or (I) resolving a mixture of isomeric compounds of formula I to isolate a specific enantiomeric form substantially in the absence of other isomers, or (J) reacting a compound of formula:

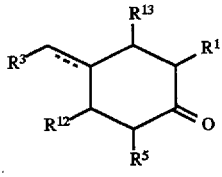
(VII)

where $R^1$, $R^3$, $R^5$ $R^{12}$, and $R^{13}$ are as defined above, with a compound of formula $R^4NH_2$ where $R^4$ is as defined above, (e.g an amine or an ammonia source such as ammonium acetate) and reducing to give a compound of formula I wherein $R^2$ is hydrogen. or (K) hydrogenating a compound of formula I where $R^4$ is a group of formula —$CR^aR^bR^c$ wherein at least one of $R^a$, $R^b$ and $R^c$ is optionally substituted aryl to give a compound of formula I wherein $R^4$ is hydrogen: or (L) alkylating a compound of formula I wherein $R^2$ is hydrogen with a halide of formula hal—$CR^aR^bR^c$ where hal is a halogen e.g. bromine to give a corresponding compound of formula I: or (M) reacting a compound of formula

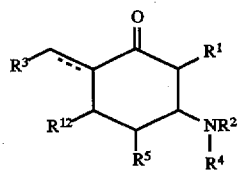

with a Grignard reagent of formula $R^{13}Mghal$ where $R^{13}$ is $C_1$-$C_6$ alkyl or $C_7$-$C_{16}$ aralkyl and hal is a halogen and reducing the product to give a corresponding compound of formula I wherein Y is —$CHR^{13}$.

Methods for carrying out processes (A)—(M) are known in the literature and may be carried out by standard procedures. If required other sites in the molecule can be protected by known methods to avoid side reactions.

Process (A) is conveniently carried out by heating in the presence of a small amount of organic base, e.g piperidine. When —$NR^2R^4$ represents NH— or a secondary amine, it is preferably protected in the form of an acetyl derivative which can be removed after reaction using basic hydrolysis.

Processes (B) and (M) may be carried out using a Grignard reagent of formula $R^3CH_2Mghal$ where hal is halogen, e.g. bromine.

Process (C) may be carried out under Wittig reaction conditions using the desired substituted triphenylphosphonium halide. Processes for carrying out Wittig reactions are extensively described in the literature. See for example Org. React. 14, 270 (1965) and Org. Syn. Coll. Vol. 5 751 (1973).

Process (D) may be carried out under Peterson reaction conditions. In the process an intermediate of formula IV in which $X^1$ is $R^3CH(OX)$— (X is Li, Na or K) is formed and this compound is hydrolysed to the alcohol and dehydrated by acid or base treatment, removing any protection groups as required. Process (E) is analogous to Process (D) and may be carried out under the same conditions.

With regard to process (F) conversions may be carried out by known means, e.g an alcohol may be formed from an ester substitutent by reduction using lithium borohydride with heating if desired in the presence of an inert solvent, e.g tetrahydrofuran. Process (F) also includes conversion of substituents on $R^4$ and/or $R^3$ when each represents an aromatic radical. Such methods are well known in the art. For example an alkoxy substiuent can be converted to hydroxy using boron tribromide. An arylmethoxy substituent can be hydrogenated to give hydroxy. Nitro substituents can be reduced to amino substituents. Amino substituents can be acylated e.g using an acyl halide to give acylaminoo or sulphonylated to give a sulphonamide, or alkylated to give an alkylamino, e.g by reductive alkylation when $R^1$ is hydrogen a Michael addition may be used to prepare compounds of formula I wherein $R^1$ —$CHR^6CHR^7CN$, —$CHR^6CHR^7COOR^8$ or —$CHR^6CHR^7CONH_2$.

Process (G) may be conveniently carried out using a reducing agent, e.g a trialkylsilane under acidic conditions such as trifluoroacetic acid. As a by-product hydroxy substitution can also occur to give a compound of formula I wherein $R^5$ is hydroxy in the 4 position.

Process (J) may be carried out by reacting a compound (VII) as defined hereinabove with an amine of formula $R^4NH_2$ to give an imine and reducing the imine. Suitable methods for reducing the imine are catalytic hydrogenation, e.g using Raney nickel and hydrogen, or using a reducing agent such as an alkali metal borohydride (e.g sodium borohydride or sodium cyanoborohydride). In the case of the latter reducing agents the reduction may be carried out simultaneously with imine formation so that the net effect is reductive animation. Raney nickel hydrogenation of 2-substituted cyclohexylimines generally gives a cis-reduced product, i.e where the hydrogen in the 1 and 2 position are both cis configuration. Borohydride reduction on the other hand gives a mixture of cis and trans configuration of hydrogens in the 1 and 2 positions.

Process (K) may be carried out by catalytic hydrogenation e.g using palladium on carbon catalyst under acidic conditions such as glacial acetic acid.

Process (L) may be carded out in an inert solvent in the presence ot a tertiary amine, e.g. $Et_3N$.

As mentioned above standard resolution techniques can be used in process (I) to isolate enantiomeric forms of the compounds of formula I. Such techniques are well known in the art.

Where necessary in the reactions described herein protecting groups may be used to protect reactive sites during a reaction and removed thereafter.

Once a compound of formula I is prepared containing a reactive substituent group or site, e.g an alkanoyloxy substituent, or an acidic proton, then such compounds may be converted to a different compound of formula I e.g hydrolysed to give corresponding hydroxy compounds of formula I. Similarly compounds of formula I containing a hydroxy group may be acylated, e.g using alkanoyl halides to give corresponding alkanoyl compounds of formula I. Similarly when an alkoxy substituent is present then such compounds may be dealkylated using standard procedures to give corresponding hydroxy compounds of formula I. Accordingly compounds of formula I may also be intermediates for other compounds of formula I.

As discussed above starting materials for the processes described herein are known compounds or can be made by analogous methods for known compounds.

For example compounds of formula (VIII) wherein $R^1$ is —$CHR^6CHR^7CN$ can be prepared by Michael addition to an enamine (formed from a cyclic ketone) as shown in Reaction Scheme I below:

Reaction Scheme I

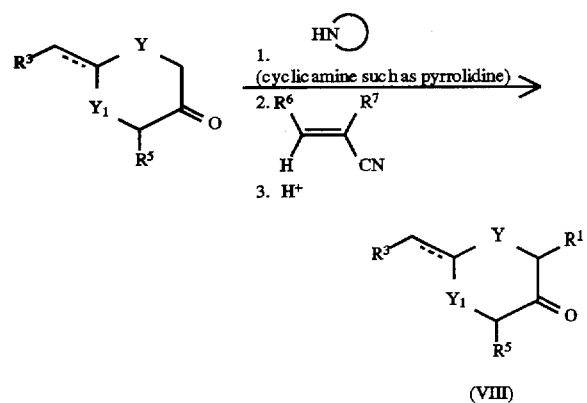

(VIII)

where $R^1$ is $CHR^6CHR^7CN$.

Similarly a compound of formula (VIII) wherein $R^1$ is —$CHR^6CHR^7COOR^8$ can be prepared by the above reaction but using an acrylic ester of formula:

(XI)

instead of an acrylonitrile.

In these two reactions Y and $Y_1$ represent —$CHR^{13}$— and $CHR^{12}$— respectively.

Compounds of formula I also possess at least two asymmetric centres and therefore isomers, enantiomers and diastereoisomers and mixtures thereof, are obtainable. Similarly E and Z isomers are obtainable when X is $R^3CH=C$. All such isomers are within the scope of this invention.

Examples of compounds of formula (1) are:
methyl (1'R,1S,2R,5R)-5-((4-methoxyphenyl)methyl-2-(1'-phenylethylamino)-cyclohexanepropionate (Example 1 ); and
methyl (1'R,1S,2R,5S )-5-((4-methoxyphenyl)methyl-2-(1'-phenylethylamino)-cyclohexanepropionate (Example 2) and its monohydrochloride salt.

The compounds of this invention may be obtained in free base form or as acid addition salts as desired. Examples of such salts include salts with pharmaceutically acceptable organic or inorganic acids such as hydrochloric, hydrobromic, hydroiodic, sulphuric, phosphoric, nitric, acetic, citric, tartaric, fumaric, succinic, malohic, formic, maleic acid or organosulphonic acids such as methane sulphonic or p-toluene sulphonic acids.

When acidic substituents are present it is also possible to form salts by treatment with bases, to give for example alkali metals (such as sodium) or ammonium salts. Such salts of the compounds of formula I are included within the scope of this invention.

When basic substituents are present then quaternary ammonium salts may be formed by quaternizing with an alkylating agent such as alkyl or aralkyl halides.

This invention also provides pharmaceutical compositions comprising a compound of formula I or a pharmaceutically acceptable salt thereof and a pharmaceutically acceptable carrier.

For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or table disintegrating agents; it can also be encapsulating material. In powders the carrier is a finely divided solid which is in admixture with the the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carrier) is surrounded by carriers, which is thus in association with it. Similarly cachets are included. Sterile liquid form compositions include sterile solutions, suspensions, emulsions, syrups and elixirs.The active ingredient can be dissolved or suspended in a pharmaceutically acceptable carrier, such a sterile water, sterile organic solvent or a mixture of both.

The active ingredients can often be dissolved in a suitable organic solvent, for instance aqueous propylene glycol containing from 10 to 75% of the glycol by weight is generally suitable. Other compositions can be made by dispersing the finely-divided active ingredient in aqueous starch or sodium carboxymethyl cellulose solution, or in a suitable oil, for instance arachis oil. The composition may be administered orally, nasally, rectally or parenterally.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 1 to 500 mg or more, e.g 25 mg to 250 mg, according to the particular need and the activity of the active ingredient. The invention also includes the compounds in the absence of carrier where the compounds are in unit dosage form. Based on the results from animal studies the dosage range for the treatment of humans using a compound of formula I will be in the range from about 1 mg to 2 g per day depending on the activity of the compound and the disease to be treated.

For certain of the abovementioned conditions it is clear that the compounds may be used prophylactically as well as for the alleviation of acute symptoms. References herein to "treatment" or the like are to be understood to include such prophylactic treatment, as well as treatment of acute conditions.

Compounds of formula I wherein one of $R^1$ and $R^5$ represents —$(CHR^6)_n CHR^7 CN$ or —$(CHR^6)_n CHR^7 COOR^8$ wherein n is 1 and $R^6$, $R^7$ and $R^8$ are as defined above are direct intermediates to pharmaceutically active compounds of formula:

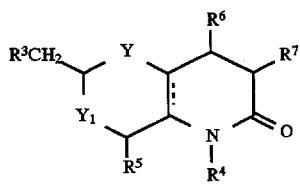

wherein $R^3$, $R^4$, $R^6$, $R^5$, $R^7$, Y and $Y_1$ the dotted line are as defined above, by cyclising a compound of formula:

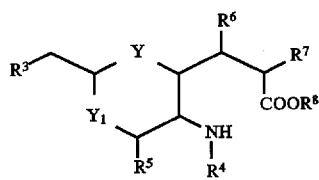

wherein $Y_1$, Y, $R^3$, $R^4$, $R^5$, $R^6$, $R^7$ and $COOR^8$ are as defined above.

The following Examples illustrate the invention and methods for preparing compounds of the invention. In the Examples relative configurations of optical centres are denoted using the R,S notation.

EXAMPLE 1

Methyl (1'R,1S,2,R5S)-5-((4-methoxyphenyl)methyl)-2-(1'-phenylethylamino-cyclohexanepropionate 2-(Methoxycarbonylethyl)-4-(4-methoxybenzyl)cyclohexanone ( t 18 g, 0.399 mol) was dissolved in toluene (1 l) with R-(+)-α-methylbenzylamine (52 g, 0.43 mol) and p-toluenesulphonic acid (0.2 g). The reaction mixture was heated under reflux in a Dean Stark apparatus for 24 hours. The solvent was removed under vacuum and the residue was hydrogenated in ethanol (800 ml) over Raney nickel at room temperature under 50 psi hydrogen for four days. The catalyst was filtered off and the solvent of the liltrate was then evaporated under vacuum. The resulting oil was then chromatographed on a silica gel with a diisopropyl ether and hexane solvent system (ratio 1:1). The first fraction yielded the title compound (50.5 g, 32% yield) which was 98% pure. A portion of the title compound (14.98 g), was converted to the dihydrochloride salt. This was achieved by dissolving in a minimum amount of diethyl ether and then diluting with hexane. Ethereal hydrochloric acid was added dropwise until precipitation was completed. The solid was filtered and washed with hexane then dried. ( 13.45 g). mp 96°–98° C., $[\alpha]_D^{25}$=+8° ( 1% MeOH).

Analysis: $C_{26}H_{35}NO_3 \cdot HCl$ requires: C, 70.01, H. 8.14; N, 3.14

Found C, 69.72; H, 8.49; N, 3.0%.

EXAMPLE 2

(−)-Methyl (1'S,1R,2S,5R)-5-(4-Methoxphenyl)methyl)-2-(1'-phenylethylamino)cyclohexanepropionate Methyl 5-(4'-methoxyphenylmethyl)-2-oxo-cyclohexanepropionate (98.5 g), with S-(−)α-methylbenzylamine in toluene (500 ml) with p-toluenesuphonic acid (0.2 g) was refluxed and water was collected by means of a Dean Stark apparatus. After 24 hours the solvent was removed under reduced pressure. The imine product was reduced in 4 batches with Raney nickel (1.2g) in ethanol (150 ml) and hydrogenated at 50 psi and 50° C. The catalyst was removed by filtration and the samples combined and purified by chromatography on silica using diisopropyl ether as eluent to give (41.91 g) of the title compound.

A sample (20.1 g) was dissolved in ether and treated with ethereal HCl. A gum was formed and the ether decanted. The gum was triturated in n-hexane to give a white solid (19.5 g), mp 110°–112° C., $[\alpha]_D^{26}$=−8°. (1% MeOH)

Analysis $C_{26}H_{35}NO_3 \cdot HCl \cdot 0.5H_2O$ requires C, 68.6; H, 8.2; N, 3.1%

Found C, 68.7; H, 8.4; N, 3.0%

EXAMPLE 3

Methyl (1'R,1S,2R,5R)-5-((4-methoxyphenyl)-2-(1'-phenylethylamino)-ethylamino)cyclohexanepropionate A. 4-Methoxybenzylcyclohexanone (43.68 g, 0.2 mol) was dissolved in toluene (250 ml). To this solution pyrrolidine (25 ml, 0.3 mol) was added together with a catalytic amount of toluene-4-sulphonic acid. The reaction mixture was refluxed with a Dean and Stark apparatus for 20 hours. Once the predicted amount of water had been collected, the solvent was removed under vacuum. Excess pyrrolidine was removed by adding a little toluene and evaporating under reduced pressure.

The resulting liquid was dissolved in methanol (200 ml) and to the resulting stirred solution methyl acrylate (18 ml, 0.2 mol) dissolved in methanol (50 ml) was added dropwise. This was stirred for 20 hours at room temperature.

The resulting liquid was neutralised with sodium bicarbonate and the product extracted into dichloromethane. The solution was then passed through a bed of Florasil. The solvent was evaporated leaving an oil. This material was purified by distillation. 2-(2-Methoxycarbonylethyl)-4-(4-methoxybenzyl)cyclohexanone distilled at 155° C., 0.05 mmHg.

B. The ketone prepared by step A (50g, 0.122 mol) was dissolved in toluene (500 ml) and R (+)-α-methylbenzylamine (18.8 g, 0.155 mol was added. The reaction mixture was heated under reflux with a Dean Stark apparatus for 24 hours. The solvent was removed under vacuum and the residue was hydrogenareal in ethanol (400 ml) over Raney nickel (5 g). The catalyst was filtered off and the solvent evaporated under vacuum. The resulting oil was then chromatographed on silica with a diisopropyl ether solvent system. The first fraction collected was identified as methyl (1'R, 1S ,2R,5S)-5-((4-methoxyphenyl)methyl)-2-

(1'-phenylethylamino)-cyclohexanepropionate (13.56 g). The second fraction collected was found to be starting material (5.02 g). The third fraction collected (8.73g) was identified as the title compound but required further purification. This was achieved using a second column run on a basic alumina in diisopropyl ether. The sample recovered as a gum was 98% pure. This was then converted to the HCl salt by dissolving the gum in the minium amount of diethyl ether, diluting it with hexane ( 100 ml) and then adding ethereal HCl until precipitation ceased. The title compound as the monohydrochloride was filtered, dried and kept under vacuum (18.5 g, mp 105°–6° C.). $[\alpha]_D^{25}=+87$ (1% MeOH)

Analysis $C_{26}H_{35}NO_3.HCl$. requires: C, 70.0: H. 8.1: N, 3.1%

Found C, 69.7; H, 8.2; N, 3.0%

EXAMPLES 4A and 4B

A) Cis-(S)-4-(4-Methoxyphenylmethyl)-N-(1'-phenylethyl)cyclohexylamine

B) Trans-(S)-4-(4-Methoxyphenylmethyl)-N-(1'-phenylethyl)cyclohexylamine

4-Methoxybenzylcyclohexanone, (5 g, 0.023 mol) was dissolved in toluene and refluxed with (S)-(−)-phenylethylamine (2.9 ml, 0.023 mol) and a catalytic amount (2 mg) of p-toluene sulphonic acid. After 20 hours when 0.4 ml of water was collected in a Dean-Stark apparatus, the solvent was evaporated under vacuum.

The imine produced was dissolved in methanol (150 ml) and cooled to −15° C. Sodium borohydride was added to the stirring solution, (0.88 g. 0.023 mol). After 2 hours the reaction was allowed to warm to room temperature. 2N HCl (5 m) was added dropwise and a white suspension formed. The solution was stirred for a further 2 hours to break down the borane complex. Ammonia was then added to neutralize the solution. The product was extracted into ether, dried and then the solvent was evaporated. Tlc showed two major spots present. These were separated on an alumina column in a 5% ethyl acetate, hexane solvent system and then converted to their corresponding hydrochloride salts.

Fraction 1 gave 1.5 g of cis-(S)-4-(4-methoxyphenylmethyl)-N-(1'-phenylethyl)-cyclohexylamine mp=223°–225° C., $[\alpha]_D^{25}=-44°$ (c=1, MeOH)

Analysis: $C_{22}H_{29}NO$. HCl requires: C, 73.4; H, 8.4; N, 3.9

Found: C, 73.5; H, 8.5; N, 3.7%

Fraction 2 gave 2.12 g of trans-(S)-4-(4-methoxyphenylmethyl)-N-(1'-phenylethyl-methyl) cyclohexylamine mp=275°–277° C., $[\alpha]_D^{25}=-47°$ (c=1, MeOH)

Analysis: $C_{22}H_{29}NO$. HCl requires: C. 73.4; H, 8.4; N. 3.9

Found: C, 73.5; H. 8.6; N. 3.9%

EXAMPLES 5A and 5B

A) Trans-(R)-4-(4-Methoxyphenylmethyl)-N-(1'Phenylethylmethyl)-cyclohexylamine

B) Cis-(R)-4-(4-Methoxyphenylmethyl)-N-(1'Phenylethylmethyl)-cyclohexylamine

4-Methoxybenzylcyclohexanone (5g, 0.023 mol) was dissolved in toluene (150 ml) and a catalytic amount (2 mg) of p-toluene sulphonic acid. After 20 hours the solvent was evaporated under vacuum. The imine produced was dissolved in methanol (50 ml) and cooled to −15° C. Sodium borohydride (0.88 g, 0.023 mol) was added to the stirred solution and after 2 hours the reaction was allowed to warm to room temperature. 1N HCl (5 ml) was added dropwise and a suspension formed. The solution was stirred for a further 2 hours and ammonia was then added to neutralize the solution. The product was extracted into diethyl ether, dried and then the solvent was evaporated. Tlc showed two major spots present. These were separated on a basic alumina column in a 5% ethyl acetate/hexane solvent system and converted to their corresponding hydrochloride salts by dissolving in diethyl ether, diluting with hexane and adding ethereal HCl.

Fraction 1: 1.1g of trans-(R)-4-(4-methoxyphenylmethyl)-N-(1'phenylethylmethyl-cyclohexylamine, hydrochloride, quarterhydrate salt, mp 275°–277° C., $[\alpha]_D^{27}=40°$ (1% in MeOH)

Analysis: $C_{22}H_{29}NO$. HCl. $0.25H_2O$ requires: C, 72.5; H, 8.4; N, 3.8

Found: C, 72.8; H, 8.4; N, 3.8%.

Fraction 2: 1.4 g of cis-(R)-4-(4-methoxyphenylmethyl)-N-(1'-phenylethylmethyl)cyclohexylamine, hydrochloride salt, mp 223°–225° C., $[\alpha]_D^{27}=34°$ (1% in MeOH)

Analysis: $C_{22}H_{29}NO$. HCl requires: C, 73.4; H, 8.4; N, 3.9

Found: C, 7.32; H, 8.2; N, 3.8%.

EXAMPLE 6

Methyl (1'S,1R,2S,5S)-5-(4-Methoxyphenyl)methyl)-2-(1-'Phenylethylamino)-Cyclohexanepropionate 2-(2-Methoxycarbonylethyl)-4-(4-methoxybenzyl) cyclohexanone (15 g, 0.049 mol) was dissolved in toluene (100 ml) with S(−)-α-methylbenzylamine (5.97 g, 0.49 mol). The reaction mixture was heated under reflux with a Dean Stark apparatus for 24 hours. The solvent was removed under vacuum and the resulting oil was hydrogenareal in ethanol (100 ml) and Raney nickel (5 g) at room temperature under 50 psi, for 4 days. The catalyst was filtered off and the solvent was then evaporated under vacuum. The resulting oil was then chromatographed on silica gel with diisopropyl ether as the solvent. The first fraction was found to be (−)-methyl-(1'S,1R,2S,5R)-5-(4-methoxyphenyl)methyt)-2-(1'-phenylethytamino)-cyclohexanepropionate. The second fraction was found to be the title compound, 7.74 g. The sample was purified on a column of basic alumina run in 10% hexane/ethyl acetate. The major fraction was collected and converted to the HCl salt of the title compound (7.95 g), mp=102°–3° C., $[\alpha]_D^{27}=-92°$ (1% methanol).

Analysis: $C_{26}H_{35}NO_3.HCl$. $0.5H_2O$ requires: C, 68.6; H, 8.2: N, 3.1%

Found: C, 68.9: H, 8.2; N, 3.1%

We claim:

1. A compound of generic formula:

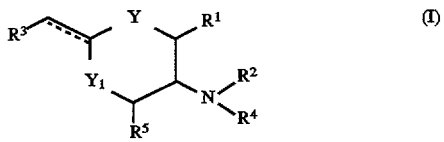

or a pharmaceutically acceptable salt thereof, where the dotted line represents an optional bond, one of $R^1$ and $R^5$ represents hydrogen, $C_1$–$C_6$ alkyl, $C_7$–$C_{16}$ aralkyl, —$(CHR^6)_n CHR^7 CN$, —$(CHR^6)_n CHR^7 CONH_2$, —$(CHR^6)_n CHR^7 COOR^8$, —$(CHR^6)_n CHR^7 CH_2 OH$ wherein n is 0 or 1, $R^6$ and $R^7$ independently represent hydrogen, $C_1$–$C_6$ alkyl- or $C_7$–$C_{16}$ aralkyl-, and $R^7$ also represents hydroxy($C_1$–$C_6$)alkyl-, ($C_2$–$C_7$)alkanoyloxy($C_1$–$C_6$)alkyl-, ($C_1$–$C_6$alkoxy)carbonyl- and $R^8$ is hydrogen or $C_1$–$C_6$ alkyl;

the other of $R^1$ and $R^5$ is hydrogen, $C_1$–$C_6$ alkyl or $C_7$–$C_{16}$ aralkyl; $R^3$ is an optionally substituted $C_6$–$C_{10}$ aryl or heteroaryl group; said heteroaryl group containing 5 to 10 ring atoms of which one or more (e.g up to 3) of said atoms are heteroatoms selected from oxygen, nitrogen and sulphur, the same or different; said aryl or heteroaryl radicals being optionally substituted by one or more substituents the same or different, eg substituents commonly used in pharmaceutical chemistry such as for example: $C_1$–$C_6$ alkyl; $C_1$–$C_6$ alkoxy or such groups substituted by $C_6$–$C_{10}$ aryl or heteroaryl as defined above; halogen; halo $C_1$–$C_6$ alkyl; halo $C_1$–$C_6$ alkoxy; carboxy; hydroxy($C_1$–$C_6$)alkyl; ($C_1$–$C_6$alkoxy)carbonyl; amino including substituted amino, e.g mono- or di- ($C_1$–$C_6$ alkyl)-amino; nitro; hydroxy; mercapto; $C_1$–$C_6$alkylthio; ($C_1$–$C_6$)alkyl carbonyl; ($C_6$–$C_{10}$ aryl)carbonyl; ($C_2$–$C_7$)alkanoyloxy; ($C_7$–$C_{11}$)aroyloxy; ($C_1$–$C_6$)alkylcarbonylamino, ($C_6$–$C_{10}$aryl)carbonylamino; ($C_2$–$C_7$) alkoxycarbonylamino; $C_6$–$C_{10}$ aryl; heteroaryl as defined above; or $C_1$–$C_2$ alkylenedioxy;

$R^2$ and $R^4$ independently represent hydrogen, or a group of formula —$CR^aR^bR^c$ where $R^a$, $R^b$ and $R^c$ are independently selected from hydrogen, $C_1$–$C_6$ alkyl, optionally substituted $C_6$–$C_{10}$ aryl, optionally substituted heteroaryl, $C_1$–$C_6$ alkyl substituted by optionally substituted $C_6$–$C_{10}$ aryl or heteroaryl in which the substituent(s) is/are for example as illustrated above in connection with $R^3$; or $R^2$ also represents $COR^{11}$ where $R^{11}$ is $C_1$–$C_6$ alkyl, $C_1$–$C_6$ alkoxy or an optionally substituted ($C_6$–$C_{10}$ aryl)alkyl or a heteroaryl alkyl radical; said heteroaryl group containing 5 to 10 ring atoms of which one or more (e.g up to 3) of said atoms are heteroatoms selected from oxygen, nitrogen and sulphur, the same or different; said aryl or heteroaryl radicals being optionally substituted by one or more substituents the same or different, eg substituents commonly used in pharmaceutical chemistry such as for example: $C_1$–$C_6$ alkyl, $C_1$–$C_6$ alkoxy, or such groups substituted by $C_6$–$C_{10}$ aryl or hetemaryl as defined above; halogen; halo $C_1$–$C_6$ alkyl, halo $C_1$–$C_6$ alkoxy; carboxy; hydroxy($C_1$–$C_6$)alkyl $C_2$–$C_7$ alkanoyloxy ($C_1$–$C_6$)alkyl; ($C_1$–$C_6$alkoxy)carbonyl; amino including substituted amino, e.g mono- or di-($C_1$–$C_6$ alkyl)-amino; nitro; hydroxy; mercapto; $C_1$–$C_6$alkylthio; ($C_1$–$C_6$alkyl)carbonyl; ($C_6$–$C_{10}$ aryl)carbonyl; ($C_2$–$C_7$) alkanoyloxy; ($C_7$–$C_{11}$)aroyloxy; ($C_1$–$C_6$alkyl)carbonylamino, ($C_6$–$C_{10}$aryl)carbonylamino; ($C_2$–$C_7$ alkoxycarbonyl)amino; $C_6$–$C_{10}$ aryl; heteroaryl as defined above; or $C_1$–$C_2$ alkylenedioxy;

one of Y and $Y_1$ is

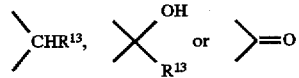

where $R^{13}$ represents hydrogen, $C_1$–$C_6$ alkyl or $C_7$–$C_{16}$ aralkyl;

the other of Y and $Y_1$ is —$CHR^{12}$— where $R^{12}$ is hydrogen, $C_1$–$C_6$ alkyl or $C_7$–$C_{16}$ aralkyl.

2. A compound as claimed in claim 1 wherein $R^4$ and $R^2$ are independently hydrogen or a group of formula —$CR^aR^bR^c$ where $R^a$ and $R^b$ are independently selected from hydrogen, methyl, ethyl, propyl, isopropyl or butyl and $R^c$ is selected from hydrogen, methyl, ethyl, isopropyl, propyl, butyl or a $C_6$–$C_{10}$ aryl or a heteroaryl group containing 5–10 ring atoms of which one or more of said atoms are heteroatoms selected from oxygen, nitrogen and sulphur in which said aryl and heteroaryl moieties are optionally substituted as defined in claim 1.

3. A compound as claimed in claim 1 wherein $R^3$ may be for example phenyl or phenyl substituted by one or more substitutents as illustrated above the same or different selected from: $C_1$–$C_6$ alkoxy, halogen, $CF_3$, $CF_3O$, $C_1$–$C_6$ alkyl, hydroxy, cyano and carboxy.

4. A compound as claimed in claim 1 wherein $Y_1$ is $CH_2$.

5. A compound as claimed in claim 1 wherein Y is $CH_2$.

6. A compound as claimed in claim 1 wherein $R^3$ is an optionally substituted phenyl or pyridyl group, said substituents being selected from: $C_1$–$C_6$ alkyl; $C_1$–$C_6$ alkoxy or such groups substituted by $C_6$–$C_{10}$ aryl or heteroaryl as defined above; halogen; halo$C_1$–$C_6$alkyl; halo$C_1$–$C_6$alkoxy; carboxy; hydroxy($C_1$–$C_6$)alkyl; ($C_1$–$C_6$alkoxy)carbonyl; amino, mono- or di- ($C_1$–$C_6$ alkyl)-amino; nitro; hydroxy; mercapto; $C_1$–$C_6$alkylthio; ($C_1$–$C_6$)alkyl carbonyl; ($C_6$–$C_{10}$ aryl)carbonyl; ($C_2$–$C_7$)alkanoyloxy; ($C_7$–$C_{11}$)aroyloxy; ($C_1$–$C_6$)alkylcarbonylamino, ($C_6$–$C_{10}$aryl)-carbonylamino; ($C_2$–$C_7$) alkoxycarbonylamino; $C_6$–$C_{10}$ aryl; heteroaryl as defined above; or $C_1$–$C_2$ alkylenedioxy.

7. A compound as claimed in claim 1 wherein $R^1$, $R^5$ and $R^6$ are hydrogen.

8. A compound of claim 1 which is methyl 5-((4-methoxyphenyl)methyl-2-(1'-phenylethylamino)-cyclohexanepropionate or a pharmaceutically acceptable salt thereof.

9. A compound of claim 1 which is methyl 5-((4-methoxyphenyl)-2-(1'-phenylethylamino)ethylamino) cyclohexanepropionate or a pharmaceutically acceptable salt thereof.

10. A compound of claim 1 which is methyl 4-(4-methoxyphenylmethyl)-N-(1'-phenylethyl)cyclohexylamine or a pharmaceutically acceptable salt thereof.

11. A compound of claim 1 which is methyl 4-(4-methoxyphenylmethyl)-N-(1'phenylethylmethyl) cyclohexylamine or a pharmaceutically acceptable salt thereof.

12. A compound of claim 1 which is methyl (1'R,1S,2R,5R)-5-((4-methoxyphenyl)methyl-2-(1'-phenylethylamino)-cyclohexanepropionate;

methyl (1'R,1S,2R,5S)-5-((4-methoxyphenyl)methyl-2-(1'-phenylethylamino)-cyclohexanepropionate;

(–)-methyl (1'S,1R,2S,5R)-5-(4-methoxyphenyl)methyl)-2-(1'phenylethylamino)-cyclohexanepropionate;

methyl (1'R,1S,2R,5R)-5-((4-methoxyphenyl)-2-(1'-phenylethylamino)ethyl-amino) cyclohexanepropionate;

cis-(S)-4-(4-methoxyphenylmethyl)-N-(1'-phenylethyl) cyclohexylamine;

trans-(S)-4-(4-methoxyphenylmethyl)-N-(1'-phenylethyl) cyclohexylamine;

trans-(R)-4-(4-methoxyphenylmethyl)-N-(1'phenylethylmethyl)cyclohexylamine;

cis-(R)-4-(4-methoxyphenylmethyl)-N-(1'phenylethylmethyl)cyclohexylamine;

or methyl (1'S,1R,2S.5S)-5-(4-methoxyphenyl)methyl)-2-(1-'phenylethylamino)-cyclohexanepropionate or a pharmaceutically acceptable salt thereof.

13. A compound of formula IA:

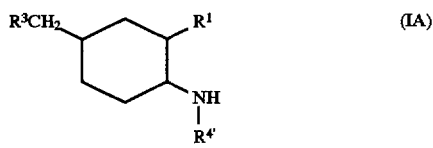

in which formula $R^1$ is hydrogen, $C_1$–$C_6$ alkyl, —$(CHR^6)_n CHR^7 CN$, —$(CHR^6)_n CHR^7 CONH_2$, —$(CHR^6)_n CHR^7 COOR^8$ or —$(CHR^6)_n CHR^7 CH_2 OH$; $R^3$ is unsubstituted or substituted phenyl where the substituents is/are selected from $C_1$–$C_6$ alkyl, $C_1$–$C_6$ alkoxy, hydroxy, halogen and methylene or ethylenedioxy; and $R^{4'}$ is hydrogen, alkyl or optionally substituted aryl($C_1$–$C_6$)alkyl in which the alkyl group is itself optionally substituted by $C_1$–$C_6$ alkyl; $R^6$ and $R^7$ independently represent hydrogen $C_1$–$C_6$ alkyl- or $C_7$–$C_{16}$ aralkyl-, and $R^7$ also represents hydroxy($C_1$–$C_6$) alkyl-, ($C_2$–$C_7$alkanoyloxy($C_1$–$C_6$)alkyl-, ($C_1$–$C_6$alkoxy) carbonyl- and $R^8$ is hydrogen or $C_1$–C6 alkyl; with the proviso that when $R^3$ is unsubstituted phenyl, then $R^1$ and $R^{4'}$ cannot both be hydrogen.

14. A compound as claimed in claim 13 wherein $R^1$ is are hydrogen, Me, Et, $^n$Pr, benzyl, —$(CH_2)_2 OH$, —$CH_2 CH_2 CN$, —$(CH_2)_2 COOMe$, and —$(CH_2)_2 COOEt$.

15. A pharmaceutical composition comprising a compound of formula

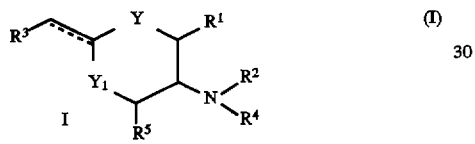

or a pharmaceutically acceptable salt thereof, where the dotted line represents an optional bond, one of $R^1$ and $R^5$ represents hydrogen, $C_1$–$C_6$ alkyl, $C_7$–$C_{16}$ aralkyl, —$(CHR^6)_n CHR^7 CN$, —$(CHR^6)_n CHR^7 CONH_2$, —$(CHR^6)_n CHR^7 COOR^8$, —$(CHR^6)_n CHR^7 CH_2 OH$ wherein n is 0 or 1, $R^6$ and $R^7$ independently represent hydrogen, $C_1$–$C_6$ alkyl- or $C_7$–$C_{16}$ aralkyl-, and $R^7$ also represents hydroxy($C_1$–$C_6$)alkyl-, ($C_2$–$C_7$)alkanoyloxy($C_1$–$C_6$)alkyl-, ($C_1$–$C_6$alkoxy) carbonyl- and $R^8$ is hydrogen or $C_1$–$C_6$ alkyl;

the other of $R^1$ and $R^5$ is hydrogen, $C_1$–$C_6$ alkyl or $C_7$–$C_{16}$ aralkyl; $R^3$ is an optionally substituted $C_6$–$C_{10}$ aryl or heteroaryl group; said heteroaryl group containing 5 to 10 ring atoms of which one or more (e.g up to 3) of said atoms are heteroatoms selected from oxygen, nitrogen and sulphur, the same or different; said aryl or heteroaryl radicals being optionally substituted by one or more substituents the same or different, eg substituents commonly used in pharmaceutical chemistry such as for example: $C_1$–$C_6$ alkyl; $C_1$–$C_6$ alkoxy or such groups substituted by $C_6$–$C_{10}$ aryl or heteroaryl as defined above; halogen; halo $C_1$–$C_6$ alkyl; halo $C_1$–$C_6$ alkoxy; carboxy; hydroxy($C_1$–$C_6$)alkyl; ($C_1$–$C_6$alkoxy) carbonyl; amino including substituted amino, e.g mono- or di- ($C_1$–$C_6$ alkyl)-amino; nitro; hydroxy; mercapto; $C_1$–$C_6$alkylthio; ($C_1$–$C_6$)alkyl carbonyl; ($C_6$–$C_{10}$ aryl)carbonyl; ($C_2$–$C_7$)alkanoyloxy; ($C_7$–$C_{11}$)aroyloxy; ($C_1$–C6)alkylcarbonylamino, ($C_6$–$C_{10}$aryl) carbonylamino; ($C_2$–$C_7$) alkoxycarbonylamino; $C_6$–$C_{10}$ aryl; heteroaryl as defined above; or $C_1$–$C_2$ alkylenedioxy;

$R^2$ and $R^4$ independently represent hydrogen, or a group of formula —$CR^a R^b R^c$ where $R^a$, $R^b$ and $R^c$ are independently selected from hydrogen, $C_1$–$C_6$ alkyl, optionally substituted $C_6$–$C_{10}$ aryl, optionally substituted heteroaryl, $C_1$–$C_6$ alkyl substituted by optionally substituted $C_6$–$C_{10}$ aryl or heteroaryl in which the substituent(s) is/are for example as illustrated above in connection with $R^3$; or $R^2$ also represents $COR^{11}$ where $R^{11}$ is $C_1$–$C_6$ alkyl, $C_1$–$C_6$ alkoxy or an optionally substituted ($C_6$–$C_{10}$ aryl)alkyl or a heteroaryl alkyl radical; said heteroaryl group containing 5 to 10 ring atoms of which one or more (e.g up to 3) of said atoms are heteroatoms selected from oxygen, nitrogen and sulphur, the same or different; said aryl or heteroaryl radicals being optionally substituted by one or more substituents the same or different, eg substituents commonly used in pharmaceutical chemistry such as for example: $C_1$–$C_6$ alkyl, $C_1$–$C_6$ alkoxy, or such groups substituted by $C_6$–$C_{10}$ aryl or heteroaryl as defined above; halogen; halo $C_1$–$C_6$ alkyl, halo $C_1$–$C_6$ alkoxy; carboxy; hydroxy($C_1$–$C_6$)alkyl $C_2$–$C_7$ alkanoyloxy ($C_1$–$C_6$)alkyl; ($C_1$–$C_6$alkoxy)carbonyl; amino including substituted amino, e.g mono- or di- ($C_1$–$C_6$ alkyl)-amino; nitro; hydroxy; mercapto; $C_1$–$C_6$alkylthio; ($C_1$–$C_6$alkyl)carbonyl; ($C_6$–$C_{10}$ aryl)carbonyl; ($C_2$–$C_7$) alkanoyloxy; (C7–$C_{11}$)aroyloxy; ($C_1$–$C_6$alkyl) carbonylamino, ($C_6$–$C_{10}$aryl)carbonylamino; ($C_2$–$C_7$ alkoxycarbonyl)amino; $C_6$–$C_{10}$ aryl; heteroaryl as defined above; or $C_1$–$C_2$ alkylenedioxy;

one of Y and $Y_1$ is

where $R^{13}$ represents hydrogen, $C_1$–$C_6$ alkyl or $C_7$–$C_{16}$ aralkyl;

the other of Y and $Y_1$ is —$CHR^{12}$— where $R^{12}$ is hydrogen, $C_1$–$C_6$ alkyl or $C_7$–$C_{16}$ aralkyl, or a pharmaceutically acceptable salt thereof and a pharmaceutically acceptable carrier.

* * * * *